US012514734B2

(12) United States Patent
Yang

(10) Patent No.: US 12,514,734 B2
(45) Date of Patent: Jan. 6, 2026

(54) FLEXIBLE AND CONVENIENTLY ADJUSTABLE NECK BRACE

(71) Applicant: Lifen Zhou, Zhejiang (CN)

(72) Inventor: Jingwei Yang, Henan (CN)

( * ) Notice: Subject to any disclaimer, the term of this patent is extended or adjusted under 35 U.S.C. 154(b) by 222 days.

(21) Appl. No.: 18/347,112

(22) Filed: Jul. 5, 2023

(65) Prior Publication Data

US 2024/0058152 A1 Feb. 22, 2024

(30) Foreign Application Priority Data

Aug. 18, 2022 (CN) ......................... 202210994309.1
Aug. 18, 2022 (CN) ......................... 202222180300.5

(51) Int. Cl.
*A61F 5/055* (2006.01)

(52) U.S. Cl.
CPC .................................... *A61F 5/055* (2013.01)

(58) Field of Classification Search
CPC .... A61F 5/055; A61F 5/04; A61F 5/05; A61F 5/048; A61F 5/028; A61F 5/05883; A61F 2005/0158; A61F 2005/0167; A61F 2005/0197
USPC ............................................................ 602/18
See application file for complete search history.

(56) References Cited

U.S. PATENT DOCUMENTS

2008/0004556 A1* 1/2008 Gehlbach ................ A61F 5/055 602/18
2021/0052412 A1* 2/2021 Wang ................... A61B 5/6803

FOREIGN PATENT DOCUMENTS

CN 111839868 A * 10/2020 ............. A61F 5/055

OTHER PUBLICATIONS

Ji et al., Translation of CN-111839868-A, Oct. 30, 2020 (Year: 2020).*

* cited by examiner

*Primary Examiner* — Daniel A Miller

(57) ABSTRACT

The invention belongs to the technical field of health care products, in particular to a flexible and conveniently adjustable neck brace, comprising a chest support block. The chest support block is connected to the adjustment components through the connection rods. The adjustment components are connected to a lower jaw support. The top of the lower jaw support is equipped with a support plate that can slide above it. The user can place head on the support plate and can rotate left and right. Compared with the existing neck brace, this structure is more flexible, and it is convenient for users to use. And it is also equipped with a magnet to facilitate the reset of the support plate to the middle position. The neck brace adopts the adjustable components, which are more convenient for users to adjust.

8 Claims, 4 Drawing Sheets

FLEXIBLE AND CONVENIENTLY ADJUSTABLE NECK BRACE

1. TECHNICAL FIELD

The invention relates to the technical field of neck health care products, in particular to a flexible and conveniently adjustable neck brace.

2. BACKGROUND ART

Neck brace is an auxiliary treatment device for cervical spondylosis. It can act as a restraint and protect the cervical spine, reduce nerve wear, alleviate traumatic reactions in the intervertebral joints, promote the reduction of tissue swelling, consolidate the therapeutic effect, and prevent recurrence. The neck brace can be applied to various types of cervical spondylosis. It is particularly suitable for patients with acute exacerbation, especially those with cervical disc herniation, sympathetic nerve type, and vertebral artery type cervical spondylosis.

However, the structure and functional design of existing neck brace are not perfect and comprehensive. For example, a neck brace and a wearable device with a neck brace with the publication number CN215937856U and the public date Mar. 4, 2022. It discloses that the utility model provides a neck brace and a wearable device with a neck brace, wherein the wearable device includes a neck brace and a head-mounted device. The head-mounted device is arranged on the neck brace. The head-mounted device is carried by the neck brace to reduce the pressure of the head-mounted device on the user's head. The neck brace includes a neck brace body and a connection unit, wherein the connection unit is arranged on the neck brace body. The head-mounted device is arranged on the connection unit, so that the connection unit carries the head-mounted device. After wearing the neck brace disclosed in this patent, it is inconvenient for the user to turn the head left and right, and the adjustable structure is not perfect, the structure is not flexible enough, the storage is inconvenient, and the adjustment of the adjustment structure is not convenient enough to operate.

3. SUMMARY OF THE INVENTION

The object of the invention is to provide a flexible and conveniently adjustable neck brace.

The object of the invention is achieved in the following way:

a flexible and conveniently adjustable neck brace, comprising a chest support block, the chest support block is connected to the adjustment components through the connection rods, one side of the adjustment component is connected to the lower jaw support, and the other side of the adjustment component is connected to the strap, the top of the lower jaw support is equipped with a support plate that can slide above it.

As a further improvement, the underside of the support plate is in contact with the smooth upper surface of the lower jaw support through several steel balls. The support plate is connected with the sliding block located on the inner arc track of the lower jaw support through the connecting piece.

As a further improvement, the front, back and bottom surfaces of the sliding block are in contact with the arc track through several steel balls. The fixed magnet embedded in the bottom of the sliding block and the magnet fixed at the bottom of the lower jaw support attract each other. The arc track is equipped with cushions on both sides to reduce the sound of sliding block hitting it.

As a further improvement, the adjustment component includes a first housing and a second housing. The first housing is provided with an arc-shaped gear rack on the edge. A hollow positioning column is arranged in the center. Both sides of the positioning column are symmetrically provided with limiting rods. The top of the positioning column is movably connected with the active ring. The active ring is connected with the lower jaw support.

As a further improvement, the active ring is provided with an actuator. The limiting rods passes through the arc-shaped limiting grooves provided on the actuator. The lower layer of the active ring is provided with spring fixing blocks. The springs fixed inside the spring fixing blocks are connected with the pawls with gear teeth. The pawls can rotate around the positioning pins and cooperate with the gear rack.

As a further improvement, both the pawls and the actuator are provided with protrusions.

As a further improvement, the tops of the connection rods are connected with the adjustment components through the Y-shaped pieces.

As a further improvement, the anti-slip teeth arranged on the inner side of the Y-shaped pieces are matched with the anti-slip teeth arranged on the surfaces of the first housing and the second housing.

As a further improvement, the Y-shaped pieces and the adjustment components are fixedly connected through the adjustment bolts. The adjustment bolts cooperate with the adjustment nuts.

Compared with the prior art, the invention has the following prominent and advantageous technical effects:

(1) The top of the lower jaw support is equipped with a support plate that can slide above it. Through the support plate, after wearing the neck brace, the user can place head on the support plate and can rotate left and right. Compared with the existing neck brace, this structure is more flexible, and it is convenient for users to use. And it is also equipped with a magnet to facilitate the reset of the support plate to the middle position.

(2) The neck brace adopts the adjustable components, which are more convenient for users to adjust. Through the adjustment components, the user only needs to adjust the lower jaw support to the top to allow the lower jaw support to be unlocked and rotated downward. Compared with the existing structural adjustment, it is more convenient to adjust.

(3) The tops of the connection rods are connected with the adjustment components through the Y-shaped pieces. Through the structural design of Y-shaped pieces, in cases where the lower jaw support is not adjusted, the angle formed by the planes of the chest support block and the lower jaw support can be adjusted by rotating the Y-shaped pieces, so that the neck brace can be adapted to more different body shapes.

4. BRIEF DESCRIPTION OF ACCOMPANY DRAWINGS

5. SPECIFIC EMBODIMENT OF THE INVENTION

The invention will be further described below in combination with specific embodiment.

Figure 1:
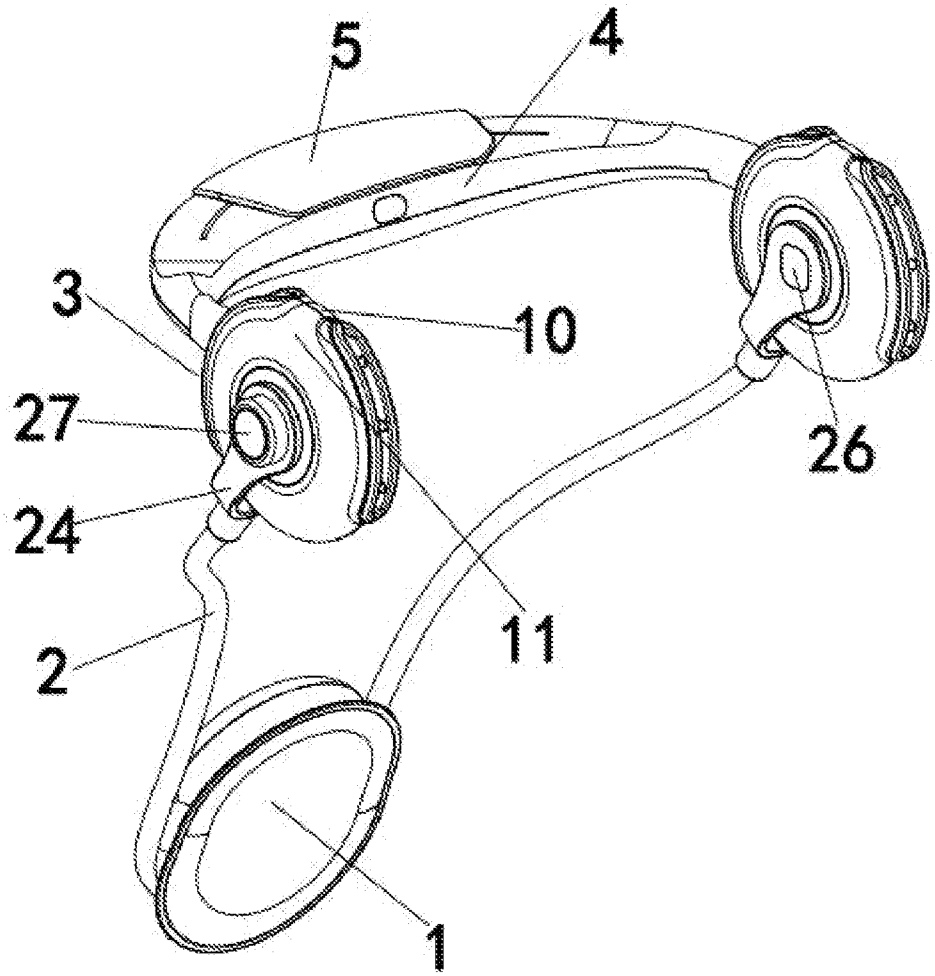
FIG. 1 is a schematic diagram of the overall structure of the invention.

As shown in FIG. 1, a flexible and conveniently adjustable neck brace, comprising a chest support block 1 against the human chest. The chest support block 1 is connected to the adjustment components 3 through the connection rods 2. The adjustment components 3 are connected to the lower jaw support 4. The adjustment components 3 are used to adjust the height of the lower jaw support 4. The top of the lower jaw support 4 is equipped with a support plate 5 that can slide above it. After the user wears the neck brace, the chin is placed on the support plate 5, and the user turns the head left and right to drive the support plate 5 to slide left and right, thereby solving the problem of not being able to turn the head or the difficult situation of turning the head after wearing the neck brace.

As shown in FIG. 1, 4, 5, the underside of the support plate 5 is in contact with the smooth upper surface of the lower jaw support 4 through several steel balls 6. The support plate 5 can slide smoothly on the surface of the lower jaw support 4 through the steel balls 6. The support plate 5 is connected with the sliding block 9 located on the inner arc track 8 of the lower jaw support 4 through the connecting piece 7. The front, back and bottom surfaces of the sliding block 9 are in contact with the arc track 8 through several steel balls 6. Through the rolling of the steel balls 6, the friction between the support plate 5 and the lower jaw support 4, the sliding block 9 and the arc track 8 can be greatly reduced, so that it is convenient for the user to turn the head. As a preference, the fixed magnet embedded in the bottom of the sliding block 9 and the magnet fixed at the bottom of the lower jaw support 4 attract each other, which helps the user to turn his head or the support plate 5 is in the middle of the lower jaw support 4 before use.

Figure 2:
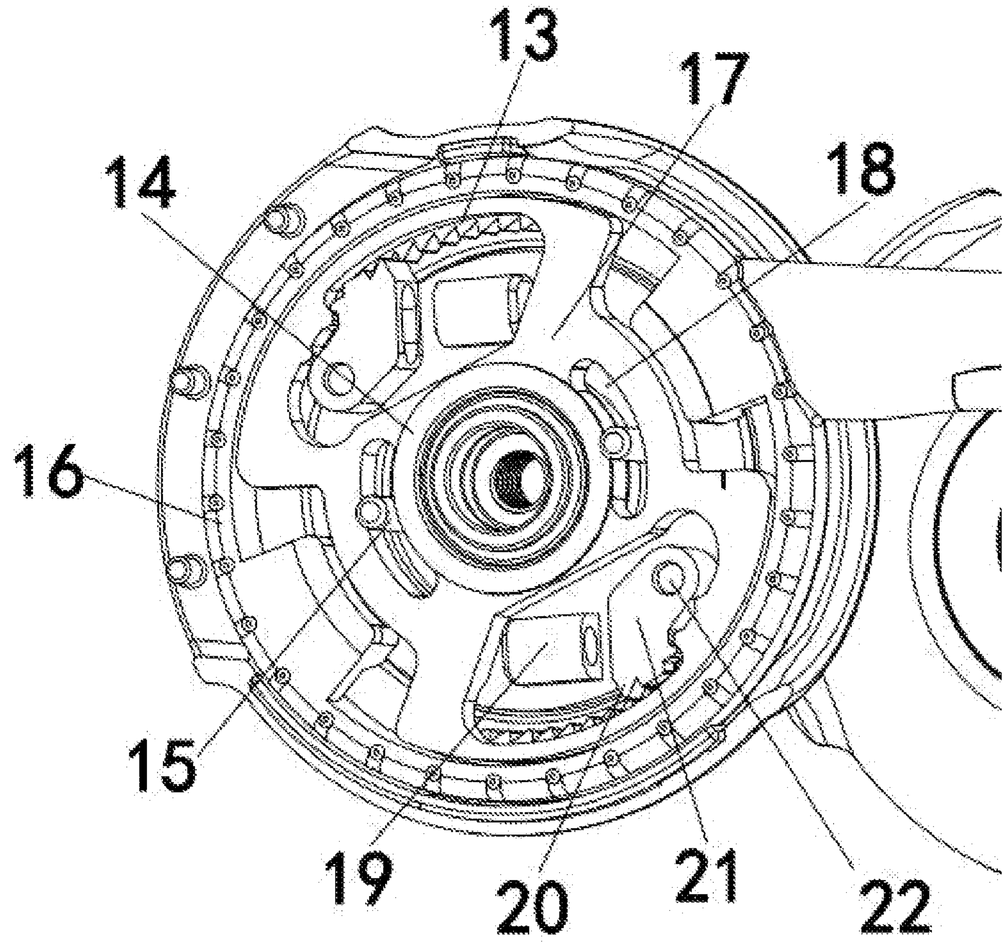
FIG. 2 is a schematic diagram of the internal structure of the adjustment component of the invention.
Figure 3:
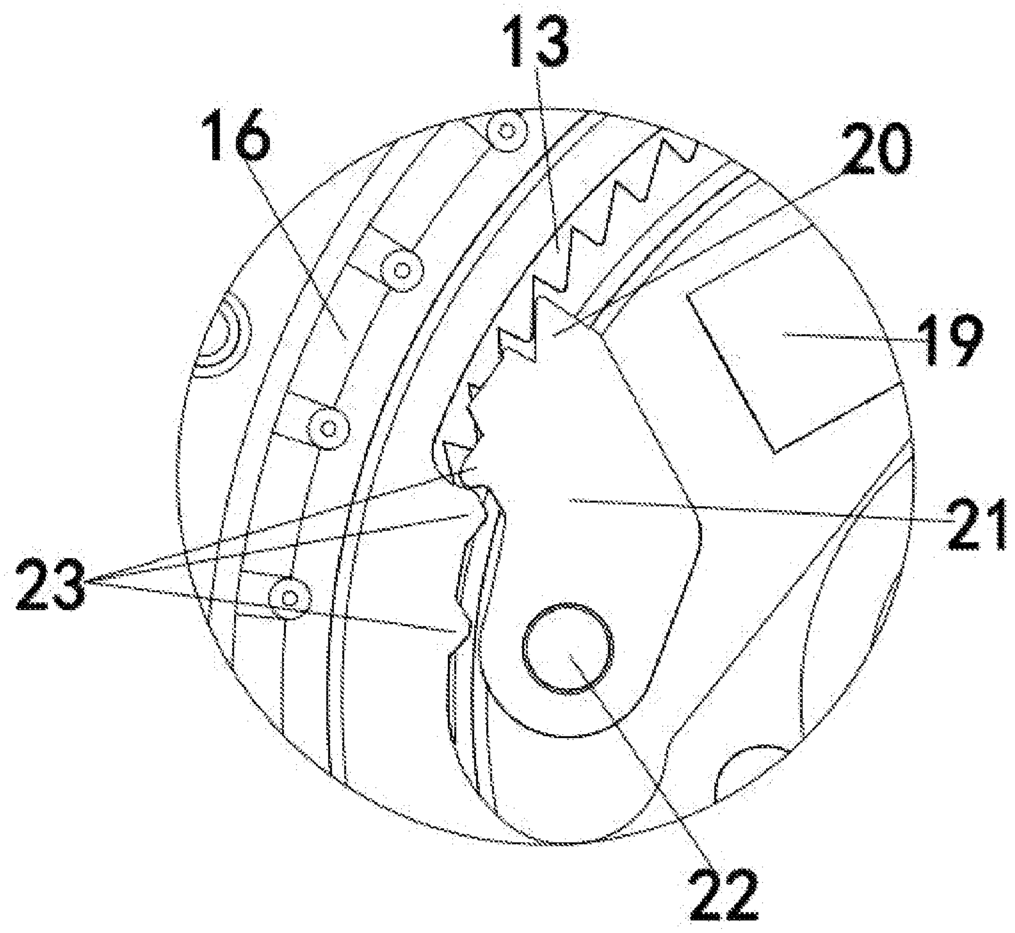
FIG. 3 is a schematic diagram of an enlarged structure of the adjustment component of the invention.
Figure 4:
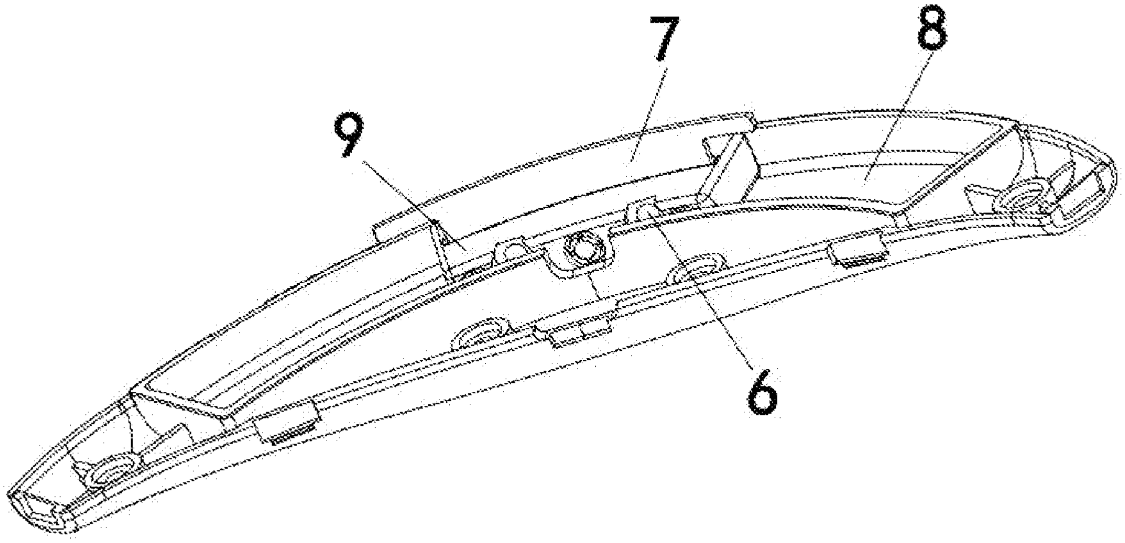
FIG. 4 is a schematic diagram of the internal structure of the lower jaw support of the invention.
Figure 5:
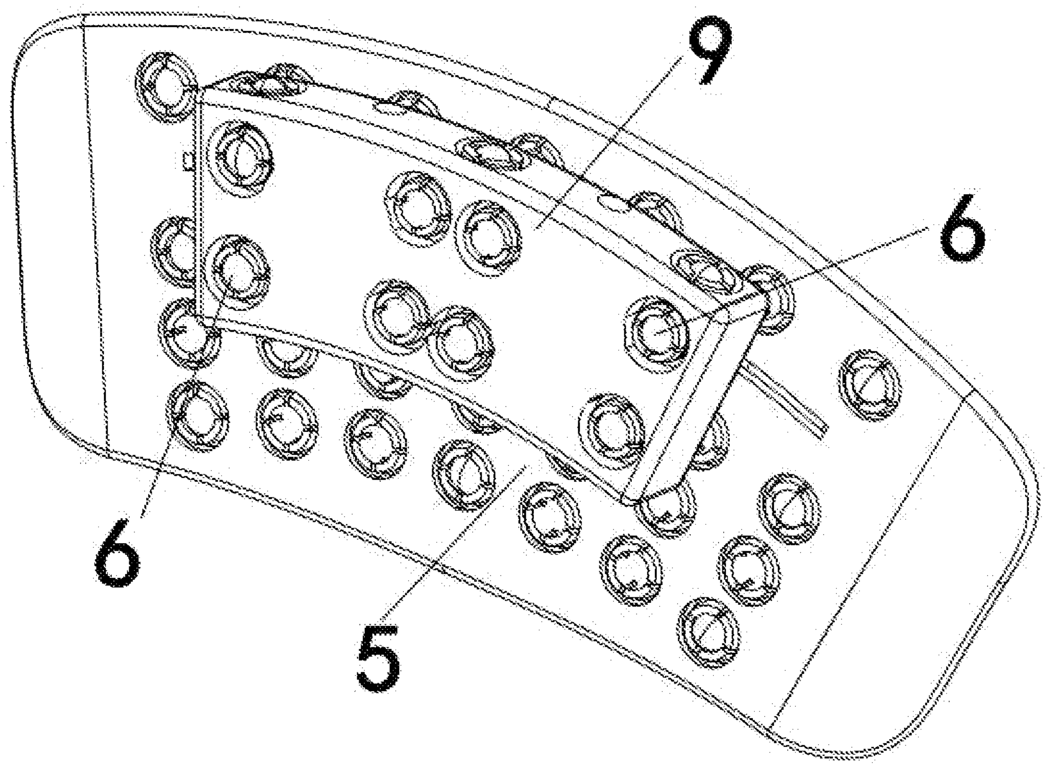
FIG. 5 is a schematic diagram of the bottom structure of the support plate of the invention.
Figure 6:
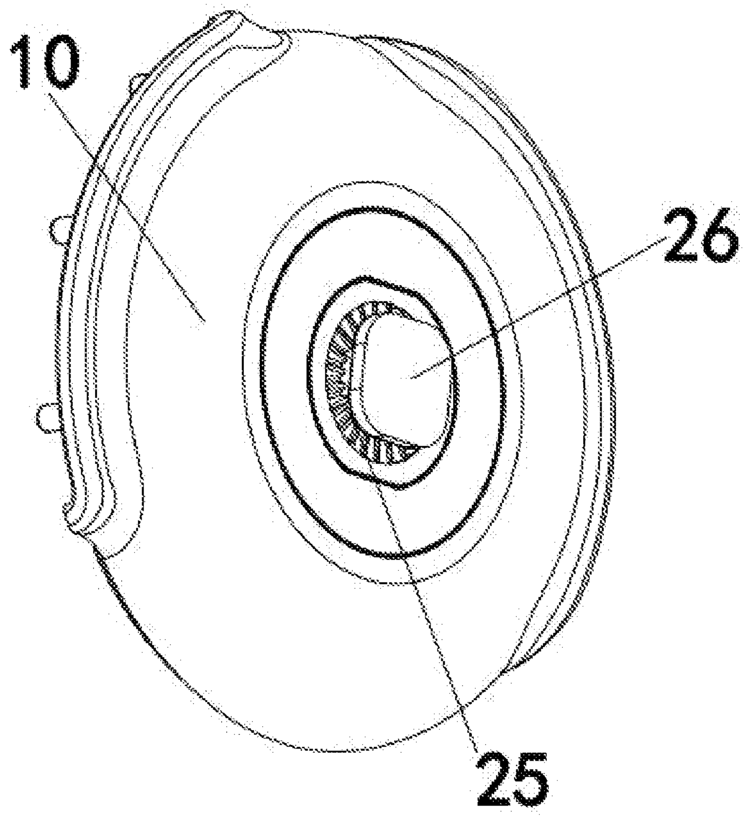
FIG. 6 is a schematic diagram of the surface of the housing of the invention.

As shown in FIG. 2, 3, the adjustment component 3 includes a first housing 10 and a second housing 11. The first housing 10 is provided with an arc-shaped gear rack 13 on the edge. The pawls 21 and the gear rack 13 adopt the structural principle of the ratchet, and the pawls 21 slides on the gear rack 13. A hollow positioning column 14 is arranged in the center. Both sides of the positioning column 14 are symmetrically provided with limiting rods 15. The top of the positioning column 14 is movably connected with the active ring 16. The active ring 16 is connected with the lower jaw support 4. The active ring 16 is provided with an actuator 17. The limiting rods 15 passes through the arc-shaped limiting grooves 18 provided on the actuator 17. The lower layer of the active ring 16 is provided with spring fixing blocks 19. The springs fixed inside the spring fixing blocks 19 are connected with the pawls 21 with gear teeth 20. The pawls 21 can rotate around the positioning pins 22 and cooperate with the gear rack 13.

When the user lifts the lower jaw support 4 up and does not reach the highest point, due to the ratchet structure principle, the pawls 21 move unidirectionally on the gear teeth 20, that is, the lower jaw support 4 can only be lifted upwards but not moved downwards. The user can adjust the lower jaw support 4 to the most suitable height according to the actual situation, so as to achieve the best treatment and correction effect. When the user finishes the use and needs to take off the neck brace, he only needs to lift the lower jaw support 4 up to the highest point by hand. At this time, the pawls 21 are under the rotation of the actuator 17, and due to the presence of protrusions 23 on both the pawls 21 and the actuator 17, the pawls 21 will rotate upward and get stuck on the actuator 17. As a result, the gear teeth 20 on the pawls 21 disengage from the gear rack 13, so that the lower jaw support 4 connected to the active ring 16 can be rotated downward, which is convenient for the user to take off the neck support. When the user needs to readjust the height of the lower jaw support 4, firstly he needs to rotate the lower jaw support 4 up to the top, and then turn the lower jaw support 4 down to the lowest part, at this time, the actuator 17 is limited by the limiting rods 15, causing the pawls 21 to move relative to the actuator 17, so that the pawls 21 can be re-cooperated with the gear rack 21. Therefore, the user can readjust the height of the lower jaw support 4.

As shown in FIG. 1, 6, the tops of the connection rods 2 are connected with the adjustment components 3 through the Y-shaped pieces 24. The anti-slip teeth 25 arranged on the inner side of the Y-shaped pieces 24 are matched with the anti-slip teeth 25 arranged on the surfaces of the first housing 10 and the second housing 11. The Y-shaped pieces 24 and the adjustment components 3 are fixedly connected through the adjustment bolts 26. The adjustment bolts 26 cooperate with the adjustment nuts 27. In actual use, the adjustment nuts 27 can be loosened by hands. In cases where the lower jaw support is not adjusted, the angles formed by the planes of the connection rods 2 and the lower jaw support 4 can be adjusted by rotating the connection rods 2 and the chest support block 1 connected to them. After adjustment is finished, tightening the adjustment nuts 27, then fixing the connection rods 2 on the first housings 10 and the second housings 11 through the Y-shaped pieces 24. Through the above structures, the adjustable range of the entire neck brace becomes larger, so that it can adapt to different groups of people.

The foregoing embodiments are only preferred embodiments of the invention, and are not intended to limit the protection scope of the invention. Therefore, all equivalent changes made according to the structure, shape, and principle of the invention should be covered within the protection scope of the invention.

The invention claimed is:

1. A flexible neck brace, comprising a chest support block (1), the chest support block (1) is connected to a pair of adjustment components (3) through a pair of connection rods (2); one side of the pair of adjustment components (3) is connected to a lower jaw support (4), and a second side of the pair of adjustment components is connected to a strap; a top of the lower jaw support (4) is equipped with a support plate (5) that can slide above the lower jaw support;

wherein:

a top of the pair of connection rods (2) are connected with the pair of adjustment components (3) through a pair of Y-shaped pieces (24).

2. The flexible neck brace of claim 1, wherein each adjustment component of the pair of adjustment components (3) includes a first housing (10) and a second housing (11), an arc-shaped gear rack (13) is provided on an edge of the first housing, a hollow positioning column (14) is arranged in a center of the first housing, a first and second side of the hollow positioning column (14) are symmetrically provided with a pair of limiting rods (15), a top of the positioning column (14) is movably connected with an active ring (16), the active ring (16) is connected with the lower jaw support (4).

3. The flexible neck brace of claim 2, wherein the active ring (16) is provided with an actuator (17), the pair of limiting rods (15) passes through a pair of arc-shaped limiting grooves (18) provided on the actuator (17), a lower layer of the active ring (16) is provided with a pair of spring fixing blocks (19), a pair of springs fixed inside of the pair of spring fixing blocks (19) are connected with a pair of pawls (21) with a set of gear teeth (20) of the arc-shaped gear rack, the pair of pawls (21) can rotated around a pair of positioning pins (22) and cooperate with the arc-shaped gear rack (13).

4. The flexible neck brace of claim 3, wherein both the pair of pawls (21) and the actuator (17) are provided with protrusions (23).

5. The flexible neck brace of claim 2, wherein a plurality of anti-slip teeth (25) arranged on an inner side of the pair of Y-shaped pieces (24) are matched with a plurality of anti-slip teeth (25) arranged on an inner and outer surface of the first housing (10) and the second housing (11).

6. The flexible neck brace of claim 1, wherein an underside of the support plate (5) is in contact with a smooth upper surface of the lower jaw support (4) through several steel balls (6); the support plate (5) is connected with a sliding block (9) located on an inner arc track (8) of the lower jaw support (4) through a connecting piece (7).

7. The flexible neck brace of claim 6, wherein a front, a back and a bottom surface of the sliding block (9) are in contact with the inner arc track (8) through the several steel balls (6).

8. The flexible neck brace of claim 1, wherein the pair of Y-shaped pieces (24) and the pair of adjustment components (3) are fixedly connected through a pair of adjustment bolts (26), the pair of adjustment bolts (26) cooperate with a pair of adjustment nuts (27).

* * * * *